United States Patent [19]

Kolberg et al.

[11] Patent Number: 5,407,795
[45] Date of Patent: Apr. 18, 1995

[54] CMV PROBES FOR USE IN SOLUTION PHASE SANDWICH

[75] Inventors: Janice A. Kolberg, Hercules; Lu-Ping Shen, San Francisco; Michael S. Urdea, Alamo, all of Calif.

[73] Assignee: Chiron Corporation, Emeryville, Calif.

[21] Appl. No.: 138,608

[22] Filed: Oct. 15, 1993

Related U.S. Application Data

[63] Continuation of Ser. No. 813,590, Dec. 23, 1991, abandoned.

[51] Int. Cl.⁶ .................. C12Q 1/70; C07H 21/02; C07H 21/04
[52] U.S. Cl. .................. 435/5; 536/23.72; 536/25.32; 536/24.3
[58] Field of Search ............ 435/5; 536/23.72, 25.32, 536/24.3; 935/77, 78

[56] References Cited

U.S. PATENT DOCUMENTS

| | | | |
|---|---|---|---|
| 4,731,325 | 3/1988 | Palva et al. | 435/5 |
| 4,762,780 | 8/1988 | Spector et al. | 435/6 |
| 4,888,105 | 9/1987 | Urdea et al. | 435/6 |
| 5,124,246 | 6/1992 | Urdea et al. | 435/5 |
| 5,175,270 | 12/1992 | Nilsen et al. | 536/24.31 |

FOREIGN PATENT DOCUMENTS

| | | |
|---|---|---|
| 0271201 | 6/1988 | European Pat. Off. . |
| 0317077 | 10/1988 | European Pat. Off. . |
| 8903891 | 5/1989 | WIPO . |
| WO91/02091 | 2/1991 | WIPO . |

OTHER PUBLICATIONS

Spaete et al. Virology 167:207–225 (1988) "Human cytomegalovirus strain . . . ".
Chou. and Dennison, *J. Infect. Dis.* (1991) 163:1229–1234.
Spector et al., *Clin. Chem.* (1989) 35(8):1581–1587.
U.S. Patent Application Ser. No. 07/558,897 (filed 27 Jul. 1990).
Chous, S.; Dennison, K. M., Analysis of interstrain variation in cytomegalovirus glycoprotein B sequences encoding neutralization–related epitopes, *J. Infect. Dis.* 163(6):1229–1234, 1991.
Spector, S. A.; Hsia, K.; Denaro, F.; Spector, D. H., Use of molecular probes to detect human cytomegalovirus and human immunodeficiency virus, *Clin. Chem.* 35(8):1581–1587, 1989.

*Primary Examiner*—Margaret Parr
*Assistant Examiner*—Eggerton Campbell
*Attorney, Agent, or Firm*—Tyler Dylan; Kenneth M. Goldman; Robert P. Blackburn

[57] ABSTRACT

Novel DNA probe sequences for detection of CMV in a sample in a solution phase sandwich hybridization assay are described. Amplified nucleic acid hybridization assays using the probes are exemplified.

9 Claims, No Drawings

SEQUENCE LISTING ( 1 ) GENERAL INFORMATION:

( i i i ) NUMBER OF SEQUENCES: 53

( 2 ) INFORMATION FOR SEQ ID NO:1:

( i ) SEQUENCE CHARACTERISTICS:
        ( A ) LENGTH: 7 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TGACTGR                                      7

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CGTGGAGACA CGGGTCCTAT GCCT                    24

( 2 ) INFORMATION FOR SEQ ID NO:3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GATGTGGTTG TCGTACTTGA TGTGGTTGTC GTACTTGATG TGGTTGTCGT ACTTGCGTAG    60

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TCCACGAAAA AAAAAA                            16

( 2 ) INFORMATION FOR SEQ ID NO:5:

( i ) SEQUENCE CHARACTERISTICS:
        ( A ) LENGTH: 12 base pairs
        ( B ) TYPE: nucleic acid ( C ) STRANDEDNESS: single
( D ) TOPOLOGY: linear ( x i ) SEQUENCE DESCRIPTION: SEQ ID NO:5:

CAGTCACTAC GC                                                                    12

( 2 ) INFORMATION FOR SEQ ID NO:6:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:6:

CCGRTTGATG TARCYGCGCA ACGTRTCRTA GGT                                              33

( 2 ) INFORMATION FOR SEQ ID NO:7:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:7:

CACACACCAR GCYTCKGCGA TYTGYGYYAR CGC                                              33

( 2 ) INFORMATION FOR SEQ ID NO:8:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:8:

TTCCYTGAAG ACCTCYAGGG W GCGCCGTTG ATC                                             33

( 2 ) INFORMATION FOR SEQ ID NO:9:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:9:

YGAGAGAATR GCTGAYGGRT TGATCTTGCT RAG                                              33

( 2 ) INFORMATION FOR SEQ ID NO:10:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:10:

GAAACGCGCG GCAATCGGTT TGTTGTARAT GGC                                              33

( 2 ) INFORMATION FOR SEQ ID NO:11:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:11:

CACGCAGCTG GCCARRCCCA RRACATCACC CAT 33

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:12:

ACGCAGCACC TTRACGCTKG TTTGGTTRAT RGT 33

(2) INFORMATION FOR SEQ ID NO:13:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:13:

GCAGCGTCCT GGCGAYTCYT TCACRTTCAT ATC 33

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:14:

GRCGAAATTA AAGATGACCA CKGGTCGYGA GTA 33

(2) INFORMATION FOR SEQ ID NO:15:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:15:

RCCCAGTTGA CCGTACTGCA CRTACGAGCT GTT 33

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:16:

GCGGTGGTTG CCCAACAGGA TTTCGTTRTC CTC 33

(2) INFORMATION FOR SEQ ID NO:17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:17:

GATCTTGAGG CTGGGAARCT GACATTCCTC AGT 33

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:18:

CACGTACTCG TAGGCCGAGT TSCCGGCGAT GAA                               33

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:19:

GCTGAGGTCA ATCATGCGTT TGAAGAGGTA GTC                               33

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:20:

YARGGCGATC ATGCTGTCGA CDGTRGAGAT RCT                               33

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:21:

CCTGAAGTCR GTRTTTCCA GCGGGTCGAT RTC                               33

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:22:

CACATATTCA TAGGCCGAGT TSCCGGCGAT GAA                               33

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:23:

CGCCACCGGC GAGATGCCGC ATAGGCGACG GAG                               33

(2) INFORMATION FOR SEQ ID NO:24:

(i) SEQUENCE CHARACTERISTICS:
        (A) LENGTH: 33 base pairs ( B ) TYPE: nucleic acid
( C ) STRANDEDNESS: single
( D ) TOPOLOGY: linear ( x i ) SEQUENCE DESCRIPTION: SEQ ID NO:24:

GCATGTCGTC CCTTCGACGT ACACTTCCTG ACG 33

( 2 ) INFORMATION FOR SEQ ID NO:25:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:25:

CGGGATGATG GTCAGCTCCT CGTAGCATTG GGC 33

( 2 ) INFORMATION FOR SEQ ID NO:26:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:26:

CTGCAGCCGC TTGTTCARCG AGCGGCCCTG ATT 33

( 2 ) INFORMATION FOR SEQ ID NO:27:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:27:

ACGGTGGACC GCTATATGGT TGCACAGCAA GCC 33

( 2 ) INFORMATION FOR SEQ ID NO:28:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:28:

CGTCTGGATA TTCACATCGG ACTGGCTTGA CGG 33

( 2 ) INFORMATION FOR SEQ ID NO:29:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:29:

GCGCGTTGTC AGGTCCAGCA GGTCCTGCTC CAC 33

( 2 ) INFORMATION FOR SEQ ID NO:30:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:30:

GAGGGCCGAA AGGACTCCAG CCAAGTGGGG GAT    33

( 2 ) INFORMATION FOR SEQ ID NO:31:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

GTGGTAGGCC GATGAAGAAG AGAATAGGCT TTT    33

( 2 ) INFORMATION FOR SEQ ID NO:32:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

CCTCAGCGCC TCCTCCGCCT CCTGGATGTA GCT    33

( 2 ) INFORMATION FOR SEQ ID NO:33:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

TCGTTCCGGT ATATCCGTAA ACAGGTTGTA CTC    33

( 2 ) INFORMATION FOR SEQ ID NO:34:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GGACCAGTAG GTAAAATCCG ACAAGGAATA TAT    33

( 2 ) INFORMATION FOR SEQ ID NO:35:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

GCCCACCCGC TTGACGATAA CCTCCGAGGT ACG    33

( 2 ) INFORMATION FOR SEQ ID NO:36:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

CTGGTGATAC ACATTTAGCT GCTGGATGGT GAT    33

( 2 ) INFORMATION FOR SEQ ID NO:37:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

GCGACTGATG CCGTTCATGA GCGCCCGGCA CAG      33

( 2 ) INFORMATION FOR SEQ ID NO:38:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

GAAGATGTCC TCCACGTCCT CCCCGTACAG ATG      33

( 2 ) INFORMATION FOR SEQ ID NO:39:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

CTCCTCCCCG TCCAACGCCT TTTCCCCGAG CAC      33

( 2 ) INFORMATION FOR SEQ ID NO:40:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

GGGGGCGGCA AAGACCGACC CCACGAACAT GCG      33

( 2 ) INFORMATION FOR SEQ ID NO:41:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

ACGCARYTCT TTCTGCGAGT AAAGTTCCAG TAC      33

( 2 ) INFORMATION FOR SEQ ID NO:42:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

CATGATCTCY TCGAGRTCAA AAACGTTGCT GGA      33

( 2 ) INFORMATION FOR SEQ ID NO:43:

( i ) SEQUENCE CHARACTERISTICS:

(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:43:

CTTTACCCGC TGCTTGTACG AGTTGAAYTC GCG    33

(2) INFORMATION FOR SEQ ID NO:44:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:44:

CGGYARCGGG TCGACTACCT TGTCCTCCAC GTA    33

(2) INFORMATION FOR SEQ ID NO:45:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:45:

GCTCATGAGG TCGTCCAGAC CCTTGAGGTA GGG    33

(2) INFORMATION FOR SEQ ID NO:46:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:46:

CTTTACCCGC TGCTTATACG AATTGAAYTC GCG    33

(2) INFORMATION FOR SEQ ID NO:47:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:47:

GCTGAGGGAT GTGATGAGGT CGATGATCCT GTT    33

(2) INFORMATION FOR SEQ ID NO:48:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO:48:

GTTGAACACC GGGTTGTCCT CGAAAGCTTG AAT    33

(2) INFORMATION FOR SEQ ID NO:49:

(i) SEQUENCE CHARACTERISTICS:
(A) LENGTH: 33 base pairs
(B) TYPE: nucleic acid
(C) STRANDEDNESS: single
(D) TOPOLOGY: linear ( x i ) SEQUENCE DESCRIPTION: SEQ ID NO:49:

TTTGGTGTAC ATCTCGTTGC TTTCGTGGAG CTT 33

( 2 ) INFORMATION FOR SEQ ID NO:50:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

CGGACGTCGA ATCTCCTCGA GAATATGCTT GAT 33

( 2 ) INFORMATION FOR SEQ ID NO:51:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:51:

AGGCATAGGA CCCGTGTCTT 20

( 2 ) INFORMATION FOR SEQ ID NO:52:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:52:

TTTGTGGG 8

( 2 ) INFORMATION FOR SEQ ID NO:53:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

CTTCTTTGGA GAAAGTGGTG 20

CMV PROBES FOR USE IN SOLUTION PHASE SANDWICH

This application is a continuation of application Ser. No. 07/813,590, filed Dec. 23, 1991, which is now abandoned.

TECHNICAL FIELD

This invention is in the field of nucleic acid hybridization assays. More specifically, it relates to novel nucleic acid probes for detecting Cytomegalovirus (CMV).

BACKGROUND ART

Cytomegalovirus (CMV) is a member of the herpes virus family, causing clinical illness of particular importance in neonates, immunocompromised, and immunosuppressed patients.

Chou and Dennison (*J. Infect. Dis.* 163:1229–1234, 1991) disclose the nucleotide sequence of part of the envelope glycoprotein B gene of human CMV that encodes epitopes recognized by virus-neutralizing monoclonal antibodies for 12 distinct clinical isolates of CMV.

U.S. Pat. No. 4,731,325, issued 15 Mar. 1988, discloses restriction fragments of CMV DNA in sandwich hybridizations assays.

U.S. Pat. No. 4,762,780, issued 9 Aug. 1988, discloses the use of restriction fragments of CMV DNA which do not cross-hybridize with human DNA for use in hybridization assays for CMV.

EPA 0271201, filed 2 Nov. 1987, discloses the use of cloned restriction fragments of CMV DNA for use in hybridization assays for CMV.

PCT WO 91/02091, filed 9 Aug. 1990, discloses probe sequences to detect and distinguish herpesviruses, including a 31 residue oligonucleotide probe sequence for CMV detection.

Spector et al. (*Clin. Chem.* 35/8:1581–1587,1989) disclose a $^{32}$P-labeled RNA probe and three single-stranded DNA oligomer capture probes complementary to mRNA encoding the CMV late matrix protein for use in a "target cycling" assay, and four 20-oligonucleotide primers and two 40-oligonucleotide probes for PCR amplification of CMV.

Commonly owned U.S. Pat. No. 4,868,105, issued 19 Sep. 1989, describes a solution phase nucleic acid sandwich hybridization assay in which analyte nucleic acid is first hybridized in solution to a labeling probe set and to a capturing probe set in a first vessel. The probe-analyte complex is then transferred to a second vessel that contains a solid-phase-immobilized probe that is substantially complementary to a segment of the capturing probes. The segments hybridize to the immobilized probe, thus removing the complex from solution. Having the analyte in the form of an immobilized complex facilitates subsequent separation steps in the assay. Ultimately, single stranded segments of the labeling probe set are hybridized to labeled probes, thus permitting the analyte-containing complex to be detected via a signal generated directly or indirectly from the label.

Commonly owned European Patent Application (EPA) 883096976 discloses a variation in the assay described in U.S. Pat. No. 4,868,105, issued 19 Sep. 1989, describes the signal generated by the labeled probes is amplified. The amplification involves the use of nucleic acid multimers. These multimers are branched polynucleotides that are constructed to have a segment that hybridizes specifically to the analyte nucleic acid or to a nucleic acid (branched or linear) that is bound to the analyte and iterations of a second segment that hybridize specifically to the labeled probe. In the assay employing the multimer, the initial steps of hybridizing the analyte to label or amplifier probe sets and capturing probe sets in a first vessel and transferring the complex to another vessel containing immobilized nucleic acid that will hybridize to a segment of the capturing probes are followed. The multimer is then hybridized to the immobilized complex and the labeled probes in turn hybridized to the second segment iterations on the multimer. Since the multimers provide a large number of sites for label probe attachment, the signal is amplified. Amplifier and capture probe sequences are disclosed for Hepatitis B virus, *Neisseria gonorrhoeae*, penicillin and tetracycline resistance in *N. gonorrhoeae*, and *Chlamydia trachomatis*.

Commonly owned U.S. application Ser. No. 558,897, filed 27 Jul. 1990, now abandoned in favor of commonly owned copending U.S. application Ser. No. 07/813,588, filed 23 Dec. 1991, describes the preparation of large comb-type branched polynucleotide multimers for use in the above-described solution phase assay. Pertinent information from U.S. Ser. No. 558,897 is disclosed below following the Examples. The combs provide greater signal enhancement in the assays than the smaller multimers.

DISCLOSURE OF THE INVENTION

One aspect of the invention is a synthetic oligonucleotide useful as an amplifier probe in a sandwich hybridization assay for CMV comprising a first segment having a nucleotide sequence substantially complementary to a segment of CMV nucleic acid, and a second segment having a nucleotide sequence substantially complementary to an oligonucleotide multimer.

Another aspect of the invention is a synthetic oligonucleotide useful as a capture probe in a sandwich hybridization assay for CMV comprising a first segment having a nucleotide sequence substantially complementary to a segment of CMV nucleic acid, and a second segment having a nucleotide sequence substantially complementary to an oligonucleotide bound to a solid phase.

Another aspect of the invention is a solution sandwich hybridization assay for detecting the presence of CMV in a sample, comprising
  (a) contacting the sample under hybridizing conditions with an excess of (i) an amplifier probe oligonucleotide comprising a first segment having a nucleotide sequence substantially complementary to a segment of CMV nucleic acid and a second segment having a nucleotide sequence substantially complementary to an oligonucleotide unit of a nucleic acid multimer and (ii) a capture probe oligonucleotide comprising a first segment having a nucleotide sequence that is substantially complementary to a segment of CMV nucleic acid and a second segment that is substantially complementary to an oligonucleotide bound to a solid phase;
  (b) contacting the product of step (a) under hybridizing conditions with said oligonucleotide bound to the solid phase;
  (c) thereafter separating materials not bound to the solid phase;
  (d) contacting the bound product of step (c) under hybridization conditions with the nucleic acid multimer, said multimer comprising at least one oligonucleotide unit that is substantially complementary to the second segment of the amplifier probe polynucleotide and a multiplicity of second oligonucleotide units that are substantially complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g).

Another aspect of the invention is a kit for the detection of CMV comprising a kit for the detection of CMV in a sample comprising in combination (i) a set of amplifier probe oligonucleotides wherein the amplifier probe oligonucleotide comprises a first segment having a nucleotide sequence substantially complementary to a segment of CMV nucleic acid and a second segment having a nucleotide sequence substantially complementary to an oligonucleotide unit of a nucleic acid multimer;

(ii) a set of capture probe oligonucleotides wherein the capture probe oligonucleotide comprises a first segment having a nucleotide sequence that is substantially complementary to a segment of CMV nucleic acid and a second segment that is substantially complementary to an oligonucleotide bound to a solid phase;

(iii) a nucleic acid multimer, said multimer comprising at least one oligonucleotide unit that is substantially complementary to the second segment of the amplifier probe polynucleotide and a multiplicity of second oligonucleotide units that are substantially complementary to a labeled oligonucleotide; and (iv) a labeled oligonucleotide.

These and other embodiments will occur to one of ordinary skill in the art in view of the disclosure herein.

MODES FOR CARRYING OUT THE INVENTION

Definitions

"Solution phase nucleic acid hybridization assay" intends the assay techniques described and claimed in commonly owned U.S. Pat. No. 4,868,105 and EPA 883096976.

A "modified nucleotide" intends a nucleotide monomer that may be stably incorporated into a polynucleotide and which has an additional functional group. Preferably, the modified nucleotide is a 5'-cytidine in which the $N^4$-position is modified to provide a functional hydroxy group.

An "amplifier multimer" intends a branched polynucleotide that is capable of hybridizing simultaneously directly or indirectly to analyte nucleic acid and to a multiplicity of polynucleotide iterations (i.e., either iterations of another multimer or iterations of a labeled probe). The branching in the multimers is effected through covalent bonds and the multimers are composed of two types of oligonucleotide units that are capable of hybridizing, respectively, to analyte nucleic acid or nucleic acid hybridized to analyte nucleic acid and to a multiplicity of labeled probes. The composition and preparation of such multimers are described in EPA 883096976 and U.S. Ser. No. 558,897, filed 27 Jul. 1990, the disclosures of which are incorporated herein by reference. U.S. Ser. No. 558,897 has been abandoned in favor of commonly owned copending U.S. application Ser. No. 07/813,588, filed 23 Dec. 1991. Pertinent information from U.S. Ser. No. 558,897, is disclosed below following the Examples.

The term "amplifier probe" is intended as a branched or linear polynucleotide that is constructed to have a segment that hybridizes specifically to the analyte nucleic acid and iterations of a second segment that hybridize specifically to an amplifier multimer.

The term "capture probe" is intended as an oligonucleotide having a segment substantially complementary to a nucleotide sequence of the target DNA and a segment that is substantially complementary to a nucleotide sequence of a solid-phase-immobilized probe.

"Large" as used herein to describe the comb-type branched polynucleotides of the invention intends a molecule having at least about 15 branch sites and at least about 20 iterations of the labeled probe binding sequence.

"Comb-type" as used herein to describe the structure of the branched polynucleotides of the invention intends a polynucleotide having a linear backbone with a multiplicity of sidechains extending from the backbone.

A "cleavable linker molecule" intends a molecule that may be stably incorporated into a polynucleotide chain and which includes a covalent bond that may be broken or cleaved by chemical treatment or physical treatment such as by irradiation.

All nucleic acid sequences disclosed herein are written in a 5' to 3' direction. Nucleotides are designated according to the nucleotide symbols recommended by the IUPAC-IUB Biochemical Nomenclature Commission.

Solution Phase Hybridization Assay

The general protocol for the solution phase sandwich hybridizations is as follows. The analyte nucleic acid is placed in a microtiter well with an excess of two single-stranded nucleic acid probe sets: (1) a set of capture probes, each having a first binding sequence substantially complementary to the analyte and a second binding sequence that is substantially complementary to nucleic acid bound to a solid support, for example, the well surface or a bead, and (2) a set of amplifier probes (branched or linear), each having a first binding sequence that is capable of specific binding to the analyte and a second binding sequence that is capable of specific binding to a segment of the multimer. The resulting product is a three component nucleic acid complex of the two probes hybridized to the analyte by their first binding sequences. The second binding sequences of the probes remain as single-stranded segments as they are not substantially complementary to the analyte. This complex hybridizes to the immobilized probe on the solid surface via the second binding sequence of the capture probe. The resulting product comprises the complex bound to the solid surface via the duplex formed by the oligonucleotide bound to the solid surface and the second binding sequence of the capture probe. Unbound materials are then removed from the surface such as by washing.

The amplification multimer is then added to the bound complex under hybridization conditions to permit the multimer to hybridize to the available second binding sequence(s) of the amplifier probe of the complex. The resulting complex is then separated from any unbound multimer by washing. The labeled oligonucleotide is then added under conditions which permit it to hybridize to the substantially complementary oligonucleotide units of the multimer. The resulting immobilized labeled nucleic acid complex is then washed to remove unbound labeled oligonucleotide, and read.

The analyte nucleic acids may be from a variety of sources, e.g., biological fluids or solids, and may be prepared for the hybridization analysis by a variety of means, e.g., proteinase K/SDS, chaotropic salts, etc. Also, it may be of advantage to decrease the average size of the analyte nucleic acids by enzymatic, physical or chemical means, e.g., restriction enzymes, sonication, chemical degradation (e.g., metal ions), etc. The fragments may be as small as 0.1 kb, usually being at least about 0.5 kb and may be 1 kb or higher. The analyte sequence is provided in single-stranded form for analysis. Where the sequence is naturally present in single-stranded form, denaturation will not be required. However, where the sequence may be present in double-stranded form, the sequence should be denatured. Denaturation can be carried out by various techniques, such as alkali, generally from about 0.05 to 0.2 M hydroxide, formamide, salts, heat, enzymes, or combinations thereof.

The first binding sequences of the capture probe and amplifier probe that are substantially complementary to the analyte sequence will each be of at least 15 nucleotides, usually at least 25 nucleotides, and not more than about 5 kb, usually not more than about 1 kb, preferably not more than about 100 nucleotides. They will typically be approximately 30 nucleotides. They will normally be chosen to bind to different sequences of the analyte. The first binding sequences may be selected based on a variety of considerations. Depending upon the nature of the analyte, one may be interested in a consensus sequence, a sequence associated with polymorphisms, a particular phenotype or genotype, a particular strain, or the like.

The number of different amplifier and capture probes used influences the sensitivity of the assay, because the more probe sequences used, the greater the signal provided by the assay system. Furthermore, the use of more probe sequences allows the use of more stringent hybridization conditions, thereby reducing the incidence of false positive results. Thus, the number of probes in a set will be at least one capture probe and at least one amplifier probe, more preferably two capture and two amplifier probes, and most preferably 5–100 capture probes and 5–100 amplifier probes.

Oligonucleotide probes for CMV were designed by aligning the DNA sequences of the glycoprotein B gene of 12 clinical strains of CMV and the laboratory-adapted strains AD169 and Towne. Additional oligonucleotide probes were designed by aligning the UL56 regions of Ad169 and Towne. Regions of greatest homology were chosen for capture probes, while regions of lesser homology were chosen as amplifier probes. Thus, as additional strains or isolates of CMV are made available, appropriate probes made be designed by aligning the sequence of the new strain or isolate with the nucleotide sequences used to design the probes of the present invention, and choosing regions of greatest homology for use as capture probes, with regions of lesser homology chosen as amplifier probes. The set of presently preferred probes and their capture or amplifier overhang regions, i.e., the regions which hybridize to sequences immobilized on solid support or to an oligonucleotide multimer, are listed in the examples.

The second binding sequences of the capture probe and amplifier probe are selected to be substantially complementary, respectively, to the oligonucleotide bound to the solid surface and to a segment of the multimer and so as to not be encountered by endogenous sequences in the sample/analyte. The second binding sequence may be contiguous to the first binding sequence or be spaced therefrom by an intermediate noncomplementary sequence. The probes may include other noncomplementary sequences if desired. These noncomplementary sequences must not hinder the binding of the binding sequences or cause nonspecific binding to occur.

The capture probe and amplifier probe may be prepared by oligonucleotide synthesis procedures or by cloning, preferably the former.

It will be appreciated that the binding sequences need not have perfect complementarity to provide homoduplexes. In many situations, heteroduplexes will suffice where fewer than about 10% of the bases are mismatches, ignoring loops of five or more nucleotides. Accordingly, as used herein the term "complementary"- 'intends exact complementarity wherein each base within the binding region corresponds exactly, and "substantially complementary" intends 90% or greater homology.

The labeled oligonucleotide will include a sequence substantially complementary to the repeated oligonucleotide units of the multimer. The labeled oligonucleotide will include one or more molecules ("labels"), which directly or indirectly provide a detectable signal. The labels may be bound to individual members of the substantially complementary sequence or may be present as a terminal member or terminal tail having a plurality of labels. Various means for providing labels bound to the oligonucleotide sequences have been reported in the literature. See, for example, Leary et al., *Proc. Natl. Acad. Sci. USA* (1983) 80:4045; Renz and Kurz, *Nucl. Acids Res.* (1984) 12:3435; Richardson and Gumport, *Nucl. Acids Res.* (1983) 11:6167; Smith et al., *Nucl. Acids. Res.* (1985) 13:2399; Meinkoth and Wahl, *Anal. Biochem.* (1984) 138:267. The labels may be bound either covalently or non-covalently to the substantially complementary sequence. Labels which may be employed include radionuclides, fluorescers, chemiluminescers, dyes, enzymes, enzyme substrates, enzyme cofactors, enzyme inhibitors, enzyme subunits, metal ions, and the like. Illustrative specific labels include fluorescein, rhodamine, Texas red, phycoerythrin, umbelliferone, luminol, NADPH, $\alpha$-$\beta$-galactosidase, horseradish peroxidase, alkaline phosphatase, etc.

The ratio of capture probe and amplifier probe to anticipated moles of analyte will each be at least stoichiometric and preferably in excess. This ratio is preferably at least about 1.5:1, and more preferably at least 2:1. It will normally be in the range of 2:1 to $10^6$:1. Concentrations of each of the probes will generally range from about $10^{-5}$ to $10^{-9}$ M, with sample nucleic acid concentrations varying from $10^{-21}$ to $10^{-12}$ M. The hybridization steps of the assay will generally take from about 10 minutes to 20 hours, frequently being completed in about 1 hour. Hybridization can be carried out at a mildly elevated temperature, generally in the range from about 20° C. to 80° C., more usually from about 35° C. to 70° C., particularly 65° C.

The hybridization reactions are usually done in an aqueous medium, particularly a buffered aqueous medium, which may include various additives. Additives which may be employed include low concentrations of detergent (0.01 to 1%), salts, e.g., sodium citrate (0.017 to 0.17 M), Ficoll, polyvinylpyrrolidone, carrier nucleic acids, carrier proteins, etc. Nonaqueous solvents may be added to the aqueous medium, such as dimethylformamide, dimethylsulfoxide, alcohols, and formamide. These other solvents are generally present in amounts ranging from 2 to 50%.

The stringency of the hybridization medium may be controlled by temperature, salt concentration, solvent system, and the like. Thus, depending upon the length and nature of the sequence of interest, the stringency will be varied.

Depending upon the nature of the label, various techniques can be employed for detecting the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectrophotometrically or visually. The various labels which have been employed in immunoassays and the techniques applicable to immunoassays can be employed with the subject assays.

Kits for carrying out amplified nucleic acid hybridization assays according to the invention will comprise in packaged combination the following reagents: the amplifier probe or set of probes; the capture probe or set of probes; the amplifier multimer; and an appropriate labeled oligonucleotide. These reagents will typically be in separate containers in the kit. The kit may also include a denaturation reagent for denaturing the analyte, hybridization buffers, wash solutions, enzyme substrates, negative and positive controls and written instructions for carrying out the assay.

The following examples further illustrate the invention. These examples are not intended to limit the invention in any manner.

EXAMPLES

Example I

Synthesis of Comb-type Branched Polynucleotide

This example illustrates the synthesis of a comb-type branched polynucleotide having 15 branch sites and sidechain extensions having three labeled probe binding sites. This polynucleotide was designed to be used in a solution phase hybridization as described in All chemical syntheses of oligonucleotides were performed on an automatic DNA synthesizer (Applied Biosystems, Inc., (ABI) model 380 B). Phosphoramidite chemistry of the beta cyanoethyl type was used including 5'-phosphorylation which employed PHOSTEL ™ reagent (DMT—O—CH$_2$CH$_2$—(SO$_2$)—CH$_2$CH$_2$—O—P(—N(iPr)$_2$)(—O—CH$_2$CH$_2$CN) wherein DMT is dimethoxytrityl and iPr is isopropyl) (ABN). Standard ABI protocols were used except as indicated. Where it is indicated that a multiple of a cycle was used (e.g., 1.2 cycle), the multiple of the standard amount of amidite recommended by ABI was employed in the specified cycle. Appended hereto are the programs for carrying out cycles 1.2 and 6.4 as run on the Applied Biosystems Model 380 B DNA Synthesizer.

A comb body of the following structure was first prepared:

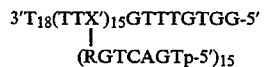

wherein X' is a branching monomer, and R is a periodate cleavable linker.

The portion of the comb body through the 15 (TTX') repeats is first synthesized using 33.8 mg aminopropyl-derivatized thymidine controlled pore glass (CPG) (2000 Å, 7.4 micromoles thymidine per gram support) with a 1.2 cycle protocol. The branching site nucleotide was of the formula:

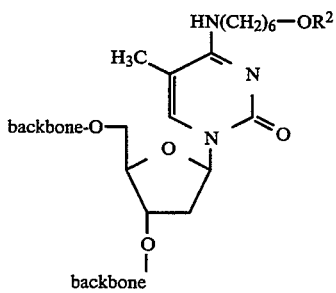

where R$^2$ represents

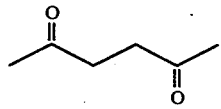

For synthesis of the comb body (not including sidechains), the concentration of beta cyanoethylphosphoramidite monomers was 0.1 M for A, C, G and T, 0.15 M for the branching site monomer E, and 0.2 M for PHOSTEL ™ reagent (DMT—O—CH$_2$CH$_2$—(SO$_2$)—CH$_2$CH$_2$—O—P(—N(iPr)$_2$)(—O—CH$_2$CH$_2$CN) wherein DMT is dimethoxytrityl and iPr is isopropyl). Detritylation was done with 3% trichloroacetic acid in methylene chloride using stepped flowthrough for the duration of the deprotection. At the conclusion the 5' DMT was replaced with an acetyl group.

Cleavable linker R and six base sidechain extensions of the formula 3'-RGTCAGTp (SEQ ID NO:1) were synthesized at each branching monomer site as follows. The base protecting group removal (R$^2$ in the formula above) was performed manually while retaining the CPG support in the same column used for synthesizing the comb body. In the case of R$^2$=levulinyl, a solution of 0.5 M hydrazine hydrate in pyridine/glacial acetic acid (1:1 v/v) was introduced and kept in contact with the CPG support for 90 min with renewal of the liquid every 15 min, followed by extensive washing with pyridine/glacial acetic acid (1:1 v/v) and then by acetonitrile. After the deprotection the cleavable linker R and six base sidechain extensions were added using a 6.4 cycle.

In these syntheses the concentration of phosphoramidites was 0.1 M (except 0.2 M R and PHOSTEL ™ reagent (DMT—O—CH$_2$CH$_2$—(SO$_2$)—CH$_2$CH$_2$—O—P(—N(iPr)$_2$)(—O—CH$_2$CH$_2$CN) wherein DMT is dimethoxytrityl and iPr is isopropyl); R was 2-(4-(4-(2-Dimethoxytrityloxy)ethyl-)phenoxy 2,3-di(-benzoyloxy)-butyloxy)phenyl)ethyl-2-cyanoethyl-N,N-diisopropylphosphoramidite).

Detritylation is effected with a solution of 3% trichloroacetic acid in methylene chloride using continuous flowthrough, followed by a rinse solution of toluene/chloromethane (1:1 v/v). Branched polynucleotide chains were removed from the solid supports automatically in the 380B using the cycle "CE NH3." The ammonium hydroxide solution was collected in 4 ml screw-capped Wheaton vials and heated at 60° C. for 12 hr to remove all base-protecting groups. After cooling to room temperature the solvent was removed in a Speed-Vac evaporator and the residue dissolved in 100 μl water.

3' backbone extensions (segment A), sidechain extensions and ligation template/linkers of the following structures were also made using the automatic synthesizer:

| | | |
|---|---|---|
| 3' Backbone extension | 3'-TCCGTATCCTGGGCACAGAGGTGCp-5' | (SEQ ID NO:2) |
| Sidechain extension | 3'-GATGCG(TTCATGCTGTTGGTGTAG)₃-5' | (SEQ ID NO:3) |
| Ligation template for linking 3' backbone extension | 3'-AAAAAAAAAAGCACCTp-5' | (SEQ ID NO:4) |
| Ligation template or linking sidechain extension | 3'-CGCATCACTGAC-5' | (SEQ ID NO:5) |

The crude comb body was purified by a standard polyacrylamide gel (7% with 7 M urea and IX TBE running buffer) method.

The 3' backbone extension and the sidechain extensions were ligated to the comb body as follows. The comb body (4 pmole/μl), 3' backbone extension (6.25 pmole/μl), sidechain extension (93.75 pmole/μl), sidechain linking template (75 pmoles/μl) and backbone linking template (5 pmole/μl) were combined in 1 mM ATP/5 mM DTT/50 mM Tris-HCl, pH 8.0/10 mM MgCl₂/2 mM spermidine, with 0.5 units/μl T4 polynucleotide kinase. The mixture was incubated at 37° C. for 2 hr, then heated in a water bath to 95° C., and then slowly cooled to below 35° C. over a 1 hr period. 2 mM ATP, 10 mM DTT, 14% polyethylene glycol, and 0.21 units/μl T4 ligase were added, and the mixture incubated for 16–24 hr at 23° C. The DNA was precipitated in NaCl/ethanol, resuspended in water, and subjected to a second ligation as follows. The mixture was adjusted to 1 mM ATP, 5 mM DTT, 14% polyethylene glycol, 50 mM Tris-HCl, pH 7.5, 10 mM MgCl₂, 2 mM spermidine, 0.5 units/μl T4 polynucleotide kinase, and 0.21 units/μl T4 ligase were added, and the mixture incubated at 23° C. for 16–24 hr. Ligation products were then purified by polyacrylamide gel electrophoresis.

After ligation and purification, a portion of the product was labeled with $^{32}$p and subjected to cleavage at the site of R achieved by oxidation with aqueous NaIO₄ for 1 hr. The sample was then analyzed by PAGE to determine the number of sidechain extensions incorporated by quantitating the radioactive label in the bands on the gel. The product was found to have a total of 45 labeled probe binding sites.

Example 2

A "15×3 amplified solution phase nucleic acid sandwich hybridization assay format was used in this assay. The "15×3" designation derives from the fact that the format employs two multimers: (1) an amplifier probe having a first segment (A) that binds to CMV and a second segment (B) that hybridizes to (2) an amplifier multimer having a first segment (B*) that hybridizes to the segment (B) and fifteen iterations of a segment (C), wherein segment C hybridizes to three labeled oligonucleotides.

The amplifier and capture probe segments and their respective names used in this assay were as follows.

| | CMV Amplifier Probes |
|---|---|
| CMV.GB.Z.1 | (SEQ ID NO:6) |
| | CCGRTTGATGTARCYGCGCAACGTRTCRTAGGT |
| CMV.GB.Z.2 | (SEQ ID NO:7) |
| | CACACACCARGCYTCKGCGATYTGYGYYARCGC |
| CMV.GB.Z.3 | (SEQ ID NO:8) |
| | TTCCYTGAAGACCTCYAGGGWGCGCCGTTGATC |
| CMV.GB.Z.4 | (SEQ ID NO:9) |
| | YGAGAGAATRGCTGAYGGRTTGATCTTGCTRAG |
| CMV.GB.Z.5 | (SEQ ID NO:10) |
| | GAAACGCGCGGCAATCGGTTTGTTGTARATGGC |
| CNV.GB.Z.6 | (SEQ ID NO:11) |
| | CACGCAGCTGGCCARRCCCARRACATCACCCAT |
| CMV.GB.Z.7 | (SEQ ID NO:12) |
| | ACGCAGCACCTTRACGCTKGTTTGGTTRATRGT |
| CMV.GB.Z.8 | (SEQ ID NO:13) |
| | GCAGCGTCCTGGCGAYTCYTTCACRTTCATATC |
| CMV.GB.Z.9 | (SEQ ID NO:14) |
| | GRCGAAATTAAAGATGACCACKGGTCGYGAGTA |
| CMV.GB.Z.10 | (SEQ ID NO:15) |
| | RCCCAGTTGACCGTACTGCACRTACGAGCTGTT |
| CMV.GB.Z.11 | (SEQ ID NO:16) |
| | GCGGTGGTTGCCCAACAGGATTTCGTTRTCCTC |
| CMV.GB.Z.12 | (SEQ ID NO:17) |
| | GATCTTGAGGCTGGGAARCTGACATTCCTCAGT |

-continued

| | |
|---|---|
| CMV.GB.Z.13a | (SEQ ID NO:18)<br>CACGTACTCGTAGGCCGAGTTSCCGGCGATGAA |
| CMV.GB.Z.14 | (SEQ ID NO:19)<br>GCTGAGGTCAATCATGCGTTTGAAGAGGTAGTC |
| CMV.GB.Z.15 | (SEQ ID NO:20)<br>YARGGCGATCATGCTGTCGACDGTRGAGATRCT |
| CMV.GB.Z.16 | (SEQ ID NO:21)<br>CCTGAAGTCRGTRTTTTCCAGCGGGTCGATRTC |
| CMV.GB.Z.13b | (SEQ ID NO:22)<br>CACATATTCATAGGCCGAGTTSCCGGCGATGAA |
| CMV.UL.22 | (SEQ ID NO:23)<br>CGCCACCGGCGAGATGCCGCATAGGCGACGGAG |
| CMV.UL.23 | (SEQ ID NO:24)<br>GCATGTCGTCCCTTCGACGTACACTTCCTGACG |
| CMV.UL.24 | (SEQ ID NO:25)<br>CGGGATGATGGTCAGCTCCTCGTAGCATTGGGC |
| CMV.UL.25 | (SEQ ID NO:26)<br>CTGCAGCCGCTTGTTCARCGAGCGGCCCTGATT |
| CMV.UL.26 | (SEQ ID NO:27)<br>ACGGTGGACCGCTATATGGTTGCACAGCAAGCC |
| CMV.UL.27 | (SEQ ID NO:28)<br>CGTCTGGATATTCACATCGGACTGGCTTGACGG |
| CMV.UL.38 | (SEQ ID NO:29)<br>GCGCGTTGTCAGGTCCAGCAGGTCCTGCTCCAC |
| CMV.UL.29 | (SEQ ID NO:30)<br>GAGGGCCGAAAGGACTCCAGCCAAGTGGGGGAT |
| CMV.UL.30 | (SEQ ID NO:31)<br>GTGGTAGGCCGATGAAGAAGAGAATAGGCTTTT |
| CMV.UL.31 | (SEQ ID NO:32)<br>CCTCAGCGCCTCCTCCGCCTCCTGGATGTAGCT |
| CMV.UL.32 | (SEQ ID NO:33)<br>TCGTTCCGGTATATCCGTAAACAGGTTGTACTC |
| CMV.UL.33 | (SEQ ID NO:34)<br>GGACCAGTAGGTAAAATCCGACAAGGAATATAT |
| CMV.UL.34 | (SEQ ID NO:35)<br>GCCCACCCGCTTGACGATAACCTCCGAGGTACG |
| CMV.UL.35 | (SEQ ID NO:36)<br>CTGGTGATACACATTTAGCTGCTGGATGGTGAT |
| CMV.UL.36 | (SEQ ID NO:37)<br>GCGACTGATGCCGTTCATGAGCGCCCGGCACAG |
| CNV.UL.37 | (SEQ ID NO:38)<br>GAAGATGTCCTCCACGTCCTCCCCGTACAGATG |
| CMV.UL.38 | (SEQ ID NO:39)<br>CTCCTCCCCGTCCAACGCCTTTTCCCCGAGCAC |
| C14V.UL.39 | (SEQ ID NO:40)<br>GGGGGCGGCAAAGACCGACCCCACGAACATGCG |
| CMV Capture Probes | |
| CMV.GB.17 | SEQ ID NO:41)<br>ACGCARYTCTTTCTGCGAGTAAAGTTCCAGTAC |
| C14V.GB.18 | (SEQ ID NO:42)<br>CATGATCTCYTCGAGRTCAAAAACGTTGCTGGA |
| CMV.GB.19a | (SEQ ID NO:43)<br>CTTTACCCGCTGCTTGTACGAGTTGAAYTCGCG |
| CMV.GB.20 | (SEQ ID NO:44)<br>CGGYARCGGGTCGACTACCTTGTCCTCCACGTA |
| CMV.GB.21 | (SEQ ID NO:45)<br>GCTCATGAGGTCGTCCAGACCCTTGAGGTAGGG |
| CMV.GB.19b | (SEQ ID NO:46)<br>CTTTACCCGCTGCTTATACGAATTGAAYTCGCG |
| CMV.UL.40 | (SEQ ID NO:47)<br>GCTGAGGGATGTGATGAGGTCGATGATCCTGTT |
| CMV.UL.41 | (SEQ ID NO:48)<br>GTTGAACACCGGGTTGTCCTCGAAAGCTTGAAT |
| CMV.UL.42 | (SEQ ID NO:49)<br>TTTGGTGTACATCTCGTTGCTTTCGTGGAGCTT |
| CMV.UL.43 | (SEQ ID NO:50)<br>CGGACGTCGAATCTCCTCGAGAATATGCTTGAT |

Each amplifier probe contained, in addition to the sequences substantially complementary to the CMV sequences, the following 5' extension complementary to a segment of the amplifier multimer,

AGGCATAGGACCCGTGTCTT (SEQ ID NO:51).

Some of the amplifier probes used in this assay also contained a sequence at their 3' end, 5'-TTTGTGGG-3' (SEQ ID NO:52), for use in other configurations of the hybridization assay. This sequence was not required for the hybridization assay as described here.

Each capture probe contained, in addition to the sequences substantially complementary to CMV DNA, a downstream sequence complementary to DNA bound to the solid phase (XT1,),

CTTCTTTGGAGAAAGTGGTG (SEQ ID NO:53).

Microtiter plates were prepared as follows. White Microlite 1 Removawell strips (polystyrene microtiter plates, 96 wells/plate) were purchased from Dynatech Inc. Each well was filled with 200 μl 1 N HCl and incubated at room temperature for 15–20 min. The plates were then washed 4 times with 1 X PBS and the wells aspirated to remove liquid. The wells were then filled with 200 μl 1 N NaOH and incubated at room temperature for 15–20 min. The plates were again washed 4 times with 1 X PBS and the wells aspirated to remove liquid.

Poly(phe-lys) was purchased from Sigma Chemicals, Inc. This polypeptide has a 1:1 molar ratio of phe:lys and an average m.w. of 47,900 gm/mole. It has an average length of 309 amino acids and contains 155 amines/mole. A 1 mg/ml solution of the polypeptide was mixed with 2M NaCl/1 X PBS to a final concentration of 0.1 mg/ml (pH 6.0). 100 μL of this solution was added to each well. The plate was wrapped in plastic to prevent drying and incubated at 30° C. overnight. The plate was then washed 4 times with 1 X PBS and the wells aspirated to remove liquid.

The following procedure was used to couple the oligonucleotide XT1, to the plates. Synthesis of XT1* was described in EPA 883096976. 20 mg disuccinimidyl suberate was dissolved in 300 μl dimethyl formamide (DMF). 26 $OD_{260}$ units of XT1* was added to 100 μl coupling buffer (50 mM sodium phosphate, pH 7.8). The coupling mixture was then added to the DSS-DMF solution and stirred with a magnetic stirrer for 30 min. An NAP-25 column was equilibrated with 10 mM sodium phosphate, pH 6.5. The coupling mixture DSS-DMF solution was added to 2 ml 10 mM sodium phosphate, pH 6.5, at 4° C. The mixture was vortexed to mix and loaded onto the equilibrated NAP-25 column. DSS-activated XT1* DNA was eluted from the column with 3.5 ml 10 mM sodium phosphate, pH 6.5. 5.6 $OD_{260}$ units of eluted DSS-activated XT1, DNA was added to 1500 ml 50 mM sodium phosphate, pH 7.8. 50 μl of this solution was added to each well and the plates were incubated overnight. The plate was then washed 4 times with 1 X PBS and the wells aspirated to remove liquid.

Final stripping of plates was accomplished as follows. 200 μL of 0.2N NaOH containing 0.5% (w/v) SDS was added to each well. The plate was wrapped in plastic and incubated at 65° C. for 60 min. The plate was then washed 4 times with 1 X PBS and the wells aspirated to remove liquid. The stripped plate was stored with desiccant beads at 2°–8° C.

Sample preparation consisted of delivering 12.5 μl P-K Buffer (2 mg/ml proteinase K in 10 mM Tris-HCl, pH 8.0/0.15 M NaCl/10 mM EDTA, pH 8.0/1% SDS/40 μg/ml sonicated salmon sperm DNA) to each well, followed by 10 μl of each sample in DMEM/10% FCS to be tested per well. A standard curve of CMV DNA was prepared by diluting stock CMV in DMEM/10% fetal calf serum (FCS) and delivering aliquots of dilutions corresponding to 5, 10, or 50 plaque forming units to wells of microtiter dishes prepared as described above. Cloned CMV DNA was also used to establish a standard curve, using 10–1000 tmoles DNA/well (1 tmole=$10^{-21}$ Mole or 602 molecules). Plates were covered and agitated to mix samples, then incubated at 65° C. to release nucleic acids.

A cocktail of the CMV-specific amplifier and capture probes listed above was added to each well (25 fmoles/well in 1 N NaOH). Plates were covered and gently agitated to mix reagents and then incubated at 65° C. for 30 min.

Neutralization buffer was then added to each well (0.77 M 3-(N-morpholino)propane sulfonic acid/1,845 M NaCl/0.185 M sodium citrate). Plates were covered and incubated for 12–18 hr at 65° C.

The contents of each well were agitated to remove all fluid, and the wells washed 2 X with washing buffer (0.1% SDS/0.015 M NaCl/0.0015 M sodium citrate).

Amplifier multimer was then added to each well (40 fmoles/well in 4 X SSC/0.1% SDS/0.5% Blocking Reagent (a purified fraction of dry milk powder, Boehringer Mannheim, catalog No. 1096 176)). After covering plates and agitating to mix the contents in the wells, the plates were incubated for 15 min at 65° C.

After a further 5–10 min period at room temperature, the wells were washed as described above.

Alkaline phosphatase label probe, disclosed in EP 883096976, was then added to each well (50 fmoles in 40 μl/well). After incubation at 55° C. for 15 min, and 5–10 min at room temperature, the wells were washed twice as above and then 3 X with 0.015 M NaCl/0.0015 M sodium citrate.

An enzyme-triggered dioxetane (Schaap et al., Tet. Lett. 191987) 28:1159–1162 and EPA Pub. No. 0254051, obtained from Lumigen, Inc., was employed. The detection procedure was as follows. 30 μl Lumiphos 530 (Lumigen) was added to each well. The wells were tapped lightly so that the reagent would fall to the bottom and gently swirled to distribute the reagent evenly over the bottom. The wells were covered and incubated at 37° C. for 40 min.

Plates were then read on a Dynatech ML 1000 luminometer. Output was given as the full integral of the light produced during the reaction.

Results are shown in the Table below. Results for each standard sample are expressed as the difference between the mean of the negative control plus two standard deviations and the mean of the sample minus two standard deviations (delta). If delta is greater than zero, the sample is considered positive. In this study, standard curves using both CMV viral particles and cloned CMV DNA were generated to demonstrate sensitivity. Additionally, host cells, CMV-positive, Herpes simplex virus (HSV)- positive, and adenovirus-positive clinical samples were tested in the assay. Each clinical sample was also diluted 10 X and tested. These results indicate the ability of these probes to distinguish CMV DNA from heterologous organisms and a sensitivity of about 5 CMV plaque forming units (pfu).

TABLE I

| SAMPLE | delta |
| --- | --- |
| Control | — |
| CMV | |
| 5 pfu | 0.23 |
| 10 pfu | 0.27 |
| 50 pfu | 1.26 |
| plasmid | |
| 10 tmole | 0.07 |
| 100 tmole | 0.58 |
| 1000 tmole | 7.99 |
| CMV+ | |
| Clinical Samples | |
| 134 | 18.96 |
| 134 (.1) | 4.40 |
| 135 | 8.09 |
| 135 (.1) | 0.82 |
| 136 | 11.85 |
| 136 (.1) | 5.01 |

TABLE I-continued

| SAMPLE | delta |
|---|---|
| 137 | 8.44 |
| 137 (.1) | 1.82 |
| 138 | 9.14 |
| 138 (.1) | 2.33 |
| 139 | 1.24 |
| 139 (.1) | 0.24 |
| 140 | 11.13 |
| 140 (.1) | 1.72 |
| 141 | 2.51 |
| 141 (.1) | 0.25 |
| Adenovirus+ Clinical samples | |
| 143 | −0.06 |
| 143 (.1) | −0.04 |
| 144 | −0.04 |
| 144 (.1) | −0.05 |
| 152 | −0.05 |
| 152 (.1) | −0.04 |
| 153 | −0.06 |
| 153 (.1) | −0.05 |
| 154 | −0.04 |
| 154 (.1) | −0.04 |
| HSV+ | |
| 117 | −0.19 |
| 117 (.1) | −0.19 |
| Host cells | |
| 118 | −0.24 |
| 118 (.1) | −0.16 |

Modifications of the above-described modes for carrying out the invention that are obvious to those of skill in biochemistry, nucleic acid hybridization assays, and related fields are intended to be within the scope of the following claims.

Procedures Involving Large Comb-Type Branched Polynucleotides

Definitions

"Large"0 as used below to describe the comb-type branched polynucleotides intends a molecule having at least about 15 branch sites and at least about 20 iterations of the labeled probe binding sequence.

"Comb-type" as used below to describe the structure of the branched polynucleotides intends a polynucleotide having a linear backbone with a multiplicity of sidechains extending from the backbone.

A "multifunctional" or "modified" nucleotide intends a nucleotide monomer which may be stably incorporated into a polynucleotide having an additional functional group, (preferably a cytosine in which the 4-position is modified to provide a functional hydroxy group), to which a nucleotide may be covalently bonded to form a sidechain.

A "cleavable linker molecule" intends a molecule that may be stably incorporated into a polynucleotide chain and which includes a covalent bond that may be broken or cleaved by chemical treatment or physical treatment such as by irradiation.

An "amplification multimer" intends a polynucleotide that is capable of hybridizing directly or indirectly to analyte nucleic acid and to a multiplicity of labeled probes.

Characterization of Large Comb-Type Branched Polynucleotides

The polynucleotide multimers are composed of a linear backbone and pendant sidechains. The backbone includes a segment that provides a specific hybridization site for analyte nucleic acid or nucleic acid bound to the analyte; whereas the pendant sidechains include iterations of a segment that provide specific hybridization sites for a labeled probe.

Preferred embodiments of these comb-type polynucleotide multimers may be represented by the following schematic formula:

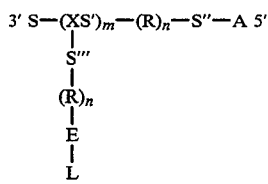

where S is a first spacer segment of at least about 15 nucleotides, preferably about 15 to 50 nucleotides, X is a multifunctional nucleotide that provides a branch site, S' is a branching site spacer segment of 0 to about 15 nucleotides, preferably 0 to 10 nucleotides, m is an integer equal to or greater than 15, preferably in the range of 15 to 100, R is a cleavable linker molecule, n is 0 or 1, S" is a second spacer segment of about 0 to 10 nucleotides, preferably 5 to 10 nucleotides, A is a segment that is capable of hybridizing specifically to analyte nucleic acid or nucleic acid bound to analyte, S''' is a third spacer segment of 0 to 10 nucleotides, E is an oligonucleotide extension of 5 to 10 nucleotides and L is a segment containing 2 to 10 iterations, preferably 3 to 6 iterations, of a nucleotide sequence that is capable of hybridizing specifically to a labeled oligonucleotide probe.

The entire backbone of the multimer or the portion thereof from S to S", inclusive, and the portion of the sidechain excluding L will typically be synthesized chemically as an integral unit using conventional automated solid-phase oligonucleotide synthesis chemistry and equipment. In this regard, the spacer segment S serves to space the portion of the molecule that contains the branching sites from the solid phase (the 3' end of S is bound to the surface of the solid phase).

The modified nucleotides or branching monomers designated X in the above formula are multifunctional nucleotides in which one functional group is used for sidechain extension and the others are used for backbone bonds. Examples of multifunctional nucleotides are described in EPA 883096976 (U.S. Ser. No. 340,031), the disclosure of which is incorporated herein by reference. These modified nucleotides are preferably of the formula:

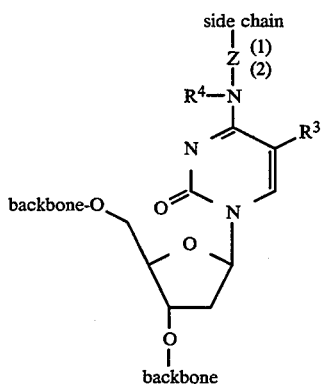

where $R^3$ is hydrogen, methyl, I, Br or F, $R^4$ is hydrogen or methyl, Z is selected from the group consisting of

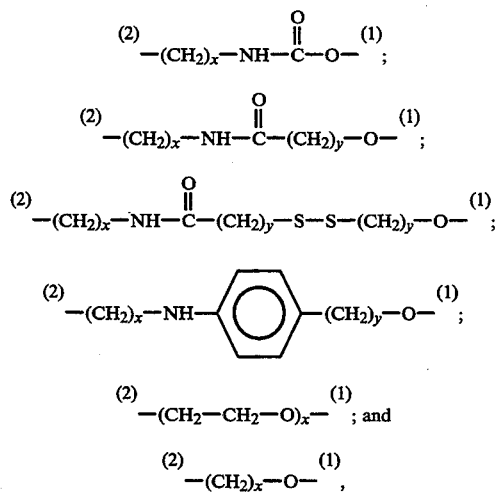

wherein x and y may be the same or different and are integers in the range of 1 to 8, inclusive. (The designations "(1)" and "(2)" at the Z linkage indicate the orientation of the Z linker moiety.)

As indicated, the spacer segment S' is optional and may be used, if desired, to space each branch site from preceding/succeeding flanking branch sites or a series of adjacent branch sites from flanking series of branch sites. The second spacer segment S" is also optional and may be employed to space the branched portion of the molecule from the segment A to which the analyte is ultimately bound. Such spacing has been found to improve the binding between the analyte and the multimer. Likewise, the third spacer segment S''' is optional. It is preferably polyT.

Segment A has a sequence and length that permits it to bind specifically and stably to the analyte or nucleic acid bound to the analyte. In order to achieve such specificity and stability segment A will normally be 15 to 50, preferably 15 to 30, nucleotides in length and have a GC content in the range of 40% to 60%. The specific length and sequence of this segment will, of course, vary depending upon the nucleic acid to which it is intended to hybridize.

Segment E is a sidechain extension that is chemically synthesized using automated solid-phase oligonucleotide synthesis equipment and techniques. It is typically about 5 to 10 nucleotides in length and serves as a site to which segment L may be ligated enzymatically.

Segment L comprises iterations of an oligomer unit that is capable of hybridizing specifically and stably to a labeled oligonucleotide probe. These units are also typically 15 to 150, preferably 20 to 120, nucleotides in length and have a GC content in the range of 40% and 60%. Each L segment will normally contain 2 to 10 iterations of the unit, preferably 3 to 6 iterations. Some sidechains may not include an L segment. Normally at least about 50% of the sidechains, preferably at least about 70% of the sidechains, will include an L segment.

The cleavable linker molecules (R) in the backbone and/or sidechains are optional, but preferred. They provide selectable cleavage sites so that samples of the large, comb-type polynucleotide may be cleaved for analysis and characterization purposes. In this regard it is preferred that there be cleavage sites in each sidechain and a cleavage site just 5' of the 5'-most branch site. Examples of cleavable linker molecules that may be incorporated into the polynucleotides are disclosed in EPA 883096976 and in the examples, infra.

Synthesis of Large Comb-Type Branched Multimers

The polynucleotides are assembled using a combination of solid phase direct oligonucleotide synthesis and enzymatic ligation methods.

The comb body, which includes the 3' spacer (S), branching sites (X), optionally the S' S" and S''' segments, the A segment, optionally the desirable linker molecules (R) and the sidechain extension E, is synthesized by automated solid phase oligonucleotide synthesis techniques. A preferred solid phase is controlled pore glass of at least 2000 Å pore size. In this synthesis spacer segment S is extended from the solid phase. For convenience, this segment is polyT. The multifunctional nucleotides that provide the branch sites are then added to the chain, with or without intervening nucleotides as spacers between branch sites. Orthogonal protecting or blocking groups are used on the modified nucleotides such that the protecting group that permits extension of the backbone may be removed without affecting the protecting group that permits sidechain extension.

Examples of appropriate protecting groups are also described in EPA 883096976. Preferably dimethoxytrityl (DMT) is used as a blocking group on the sugar moiety of the nucleotide. Levulinyl or an anthraquinonyl group of the following formula:

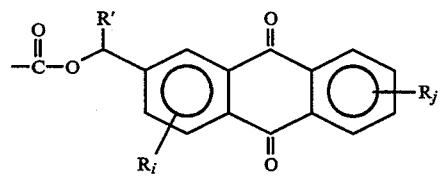

in which R' is hydrogen, aryl, or aralkyl, the $R_i$ may be the same or different and are selected from the group consisting of amino, nitro, halo, hydroxyl, lower alkyl and lower alkoxy; the $R_j$ may be the same or different and are selected from the group consisting of amino, nitro, halo, hydroxyl, lower alkyl and lower alkoxy; i is 0, 1, 2 or 3; and j is 0, 1, 2, 3 or 4, is preferably used as the blocking group on the hydroxyl moiety of the modified nucleotides. After the desired number of branch sites are incorporated, the 5' end of the molecule is extended with the S" (optional) and A segments or simply with a short S" segment (5-10 nucleotides) that provides a site for the enzymatic ligation of the A segment thereto. As indicated above, a selectable cleavage site is preferably incorporated in the extension. If the A segment is synthesized directly rather than being added by ligation, a protecting group, such as 2-methylanthraquinonyl, which may be removed selectively without adversely affecting the rest of the molecule should be used to protect the sidechain sites of the modified nucleotides.

After the 5' end of the comb body has been extended as desired, the groups protecting the hydroxyl moiety of the modified nucleotides are removed and the branching sites are extended simultaneously, preferably with the inclusion of a selectable cleavage site, so that each branch site has at least the 5–10 nucleotide extension (E) that serves as a ligation site.

The L segments (and, if not directly synthesized, the A segment, too) are then ligated to the sidechain extensions by the addition of T4 ligase and appropriate linker templates. The A and L segments and the templates may also be synthesized using available automated solid phase oligonucleotide synthesis equipment and procedures.

Example A-1

This example illustrates the synthesis of a comb-type branched polynucleotide having 15 branch sites and sidechain extensions having three labeled probe binding sites. This polynucleotide was designed to be used in a solution phase hybridization as described in EPA 883096976.

All chemical syntheses of oligonucleotides were performed on an automatic DNA synthesizer (Applied Biosystems, Inc., (ABI) model 380 A/B). Phosphoramidite chemistry of the methoxy type was used except for 5'-phosphorylation which employed Phostel ™ reagent (ABN). Standard ABI protocols were used except as indicated. Where it is indicated that a multiple of a cycle was used (e.g., 1.5 X cycle, 4.5 X cycle), the multiple of the standard amount of amidite recommended by ABI was employed in the specified cycle. Appended hereto are the programs for carrying out cycles 0.4, 1.5, 4.5, and CAP-PRIM as run on the Applied Biosystems Model 380 A/B DNA Synthesizer.

A comb body of the following structure was first prepared:

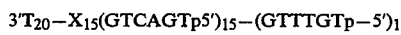

3'T$_{20}$—X$_{15}$(GTCAGTp5')$_{15}$—(GTTTGTp—5')$_1$ where X is a modified nucleotide as described previously.

The portion of the comb body through the 15 repeats is first synthesized using 40 mg thymidine controlled pore glass (CPG) (3000 Å, 3 micromoles thymidine per gram support) with a 1.5 X cycle protocol. The branching site nucleotide was of the formula:

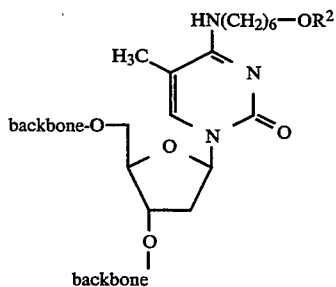

where R$^2$ represents

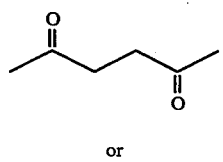

or

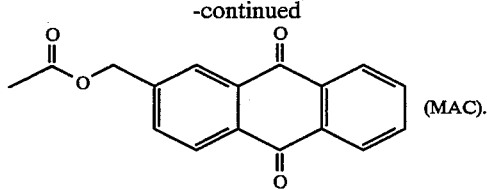

(MAC).

The monomer where R$^2$ represents MAC was made as follows. To a solution of N-4-(6-hydroxyhexyl)-5'-DMT-5-methyl-2'deoxycytidine (17 mmole), prepared as previously described (Horn and Urdea, NAR vol. 17:17, p. 6959–6967 (1989)), in 200 ml methylene chloride was added pyridine (40 mmole) and the mixture cooled to 0° C. A solution of 2-anthraquinonemethoxy chloroformate (MAC—Cl) (20 mmole) in 200 ml of CH$_2$Cl$_2$ was added dropwise and left stirring for 10 minutes. TLC analysis (silica plates developed with 10% methanol/CH$_2$Cl$_2$) showed that the starting material had been completely consumed. The reaction mixture was diluted with 400 ml ethyl acetate and the organic phase extracted with 2×300 ml 5% NaHCO$_3$ and 80% saturated aqueous NaCl. After drying of the organic phase over Na$_2$SO$_4$ for 30 minutes followed by filtration the solvent was removed in vacuo. The product was purified by silica gel chromatography using a gradient of methanol (0–6%) in CH$_2$Cl$_2$ to give 13 g of pure product (85% yield).

A 0.1 molar solution of 2-(hydroxymethyl)anthraquinone (MAQ—OH) was prepared by dissolving 25 mmole (5.95 g) in 250 ml dioxane. The yellow solution was filtered and the solvent removed by evaporation to remove water. The residue was redissolved in 200 ml dioxane and pyridine (2 ml; 25 mmole) was added. This solution was added dropwise to a stirred solution of triphosgen (2.5 g; 25 Meq) in 50 ml CH$_2$Cl$_2$. After ended addition the mixture was stirred at 20° C. for 18 hours. The mixture was diluted with 800 ml ethyl acetate and the organic phase washed with 3×60 ml 80% saturated aqueous NaCl solution. After drying of the organic phase over Na$_2$SO$_4$ the solvent was removed in vacuo to give a yellow solid, which was dissolved in CH$_2$Cl$_2$ (250 ml; 0.1 M). This solution was used without further purification.

The nucleoside N-4-(O-anthraquinonemethoxy carbonyl-6-oxyhexyl)-5'-DMT-5-methyl-2'-deoxycytidine (14.4 mmole) was dissolved in CH$_2$Cl$_2$ (50 ml) containing 70 mmole DiPEA. After cooling to 0° C. N,N-diisopropylaminomethoxychlorophosphine was added (2.72 ml; 14 mmole). The phosphitylating agent was added in small portions until 95% of the starting material had been consumed. The reaction mixture was then diluted with ethyl acetate (300 ml), extracted with 2×300 ml 5% NaHCO$_3$ then 2×300 ml 80% saturated aqueous NaCl and finally dried over solid Na$_2$SO$_4$. The solvent was removed in vacuo.

The crude phosphoramidite was purified by silica gel chromatography. The purified phosphoramidite was dissolved in toluene and added with rapid stirring to 800 ml of cold hexanes (−50° C.). The resulting precipitate was rapidly collected by filtration and dried in high vacuum for 18 hours to give 12.4 g (4.5 mmole, 80% yield) of a slightly yellow solid product. Deprotection of the MAC protected nucleotide is effected by treatment with sodium dithionite under neutral conditions.

For synthesis of the comb body (not including sidechains), the concentration of methylphosphoramidite monomers is 0.1 M for A, C, G and T, 0.15 M for the branching site monomer X, and 0.2 M for Phostel ™ reagent. Detritylation was done with 3% trichloroacetic acid in methylene chloride using continuous flowthrough for the duration of the deprotection. At the conclusion the 5′ DMT was replaced with an acetyl group.

Six base sidechain extensions of the formula 3′-GTCAGTp were synthesized at each branching monomer site as follows. The base protecting group removal ($R^2$ in the formula above) was performed manually while retaining the CPG support in the same column used for synthesizing the comb body. In the case of $R^2$=levulinyl, a solution of 0.5 M hydrazine hydrate in pyridine/glacial acetic acid (1:1 v/v) is introduced and kept in contact with the CPG support for 90 min with renewal of the liquid every 15 min. After extensive washing with pyridine/glacial acetic acid (4:1 v/v) followed by acetonitrile, the filters in the column are replaced. In the case of $R^2$=2-methylanthraquinonyl a sodium dithionite solution (1 g sodium dithionite dissolved in 20 ml of 1 M trimethylammonium bicarbonate, followed by addition of 20 ml of dioxane is introduced and kept in contact with the CPG support for 90 min. After the deprotection the six base sidechain extensions were added using a 4.5 X cycle and monomer concentrations of 0.2 M.

In these syntheses the concentration of monomers is 0.2 M (including R and Phostel ™ reagent). Detritylation is effected with a solution of 2.5% dichloroacetic acid in toluene/30% trichloroacetic acid in methylene chloride (1:1 v/v) using continuous flowthrough. Protecting groups were removed as follows. The phosphate protecting groups were removed from the solid-supported product fragment by treatment of the CPG with a solution of thiophenol/triethylamine/acetonitrile (1:1:2 v/v) for 1 hr at 20° C. followed by washes with acetonitrile (10×1 ml) and methanol. The product fragment was removed from the CPG support by treatment with 0.5 ml concentrated ammonium hydroxide for 20 min and the supernatant was removed. The treatment was repeated twice for a total of one hour exposure. The combined supernatant was transferred to a screw-capped vial and heated at 60° C. for 18 hr. After cooling to room temperature the solvent was removed in a Speed-Vac evaporator and the residue dissolved in 100 μl water.

5′ backbone extensions (segment A), sidechain extensions and ligation template/linkers of the following structures were also made using the automatic synthesizer:

| 5′ Backbone extension | 3′-AGGTGCTCCGTATCCTGGGCACAG-5′ |
| --- | --- |
| Sidechain extension | 3′-GATGCGR(TTCATGCTGTTGGTGTAG)₃-5′ |
| Ligation template for linking 5′ backbone extension | 3′-GCACCTACAAAC-5′ |
| Ligation template for linking sidechain extension | 3′-CGCATCACTGAC-5′ |

R in the sidechain extension represents the following selectable cleavage linker:

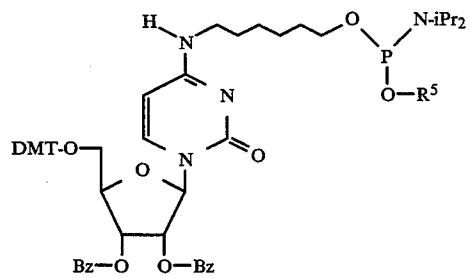

where DMT represents dimethoxytrityl, Bz represents benzoyl, $R^5$ represents methyl or β-cyanoethyl, and iPr represents isopropyl.

Cleavage at the site of R is achieved with a two-step chemical procedure: (1) oxidation with aqueous $NaIO_4$ for 1 hr followed by (2) treatment with aqueous n-propylamine.

The crude comb body was purified by a standard polyacrylamide gel (10% with 7 M urea) method.

The 5′ backbone extension and the sidechain extensions were ligated to the comb body using a standard T4 ligase protocol (Urdea (1987) Methods in Enzymol. 146:22–41), except that a longer reaction time (>8 hr), 14% polyethylene glycol, and ambient temperature are used.

After ligation and purification, a portion of the product was labeled with $^{32}p$ and subjected to the cleavage steps described above. The sample was then analyzed by PAGE to determine the number of sidechain extensions incorporated by counting the number of bands on the gel. The product was found to have a total of 24 labeled probe binding sites.

Example A-2

This example illustrates the preparation of the same multimer as made in Example A-1 using a medium pore size CPG/higher loading CPG which is first adjusted to a suitable loading level. Primary synthesis was performed starting from 30 mg thymidine CPG support (1000 Å; 20 mmoles thymidine per gram support). The first 20 coupling cycles with T were performed with the 0.4 X cycle to decrease the loading to below ca. 10 mmoles per gram support. This was followed by 20 coupling cycles with T, 15 cycles with X (modified nucleotide), and finally incorporation of the sequence 3′-GTTTGTGGp using the 1.5 X cycle. The terminal 5′-DMT group was removed and the sequence capped using the CAP-PRIM cycle program on the ABI machine. The column was removed from the machine and the following manipulations performed manually. Removal of the branch-point levulinate protecting groups was performed as described above, and the resulting CPG support transferred to a new ABI column. Sidechain extension was performed as described above to incorporate the sequence 3′-GTCAGTp using the 4.5 X cycle. The protecting groups were removed as described in Example A-1 (see above) and the crude product dissolved in 100 μl water. Ligation of the A and L groups was performed as in Example A-1.

Example A-3

The 24-site comb-type branched polynucleotide of Example A-1 was used in a solution phase sandwich assay for *N. gonorrhoeae* using pilin gene-specific capture and amplifier probes and both $^{32}p$ and alkaline phosphatase-labeled probes as described in Example 5 of EPA 883096976. The two types of labels were used to assess whether use of a 24-site comb structure using alkaline phosphatase labeled probes gave any steric problems. Results were compared to those using a 5-site comb structure which had not exhibited any steric hindrance problems.

When a $^{32}p$ probe was used, the 24 site molecule gave an increase in relative output over the standard 5 site comb of 4.76 (theoretical 4.8; 195,000±10,000 CPM versus 41,000±1,200 CPM, respectively, at 10 attomoles). When an alkaline phosphatase labeled probe was employed, the 24 site molecule gave an increase in relative output over the standard 5 site comb of 3.94 (50.1±1.7 light counts, LC, versus 12.7±0.2 LC, respectively at 10 attomoles). The difference in labeling efficiency with the two types of probes indicates that the enzyme label is accommodated well in the comb structure.

---

We claim:

1. A synthetic oligonucleotide useful as an amplifier probe in a sandwich hybridization assay for cytomegalovirus consisting of:

a first segment having a minimum length of about 25 nucleotides and a maximum length of about 1.000 nucleotides comprising a nucleotide sequence substantially complementary to a segment of cytomegalovirus nucleic acid; and a second segment consisting of a nucleotide sequence which is substantially complementary to an oligonucleotide multimar but not complementary to cytomegalovirus nucleic acid, and optionally one or more non-complementary segments each consisting of a nucleotide sequence that is not complementary to cytomegalovirus nucleic acid;

wherein said nucleotide sequence substantially complementary to a segment of cytomegalovirus nucleic acid is selected from the group consisting of the sequences CCGRTTGATGTARCYGCGCAACGTRTCRTAGGT, (SEQ ID NO:6)
CACACACCARGCYTCKGCGATYTGYGYYARCGC, (SEQ ID NO:7)
TTCCYTGAAGACCTCYAGGGWGCGCCGTTGATC, (SEQ ID NO:8)
YGAGAGAATRGCTGAYGGRTTGATCTTGCTRAG, (SEQ ID NO:9)
GAAACGCGCGGCAATCGGTTTGTTGTARATGGC, (SEQ ID NO:10)
CACGCAGCTGGCCARRCCCARRACATCACCCAT, (SEQ ID NO:11)
ACGCAGCACCTTRACGCTKGTTTGGTTRATRGT, (SEQ ID NO:12)
GCAGCGTCCTGGCGAYTCYTTCACRTTCATATC, (SEQ ID NO:13)
GRCGAAATTAAAGATGACCACKGGTCGYGAGTA, (SEQ ID NO:14)

-continued

RCCCAGTTGACCGTACTGCACRTACGAGCTGTT, (SEQ ID NO:15)
GCGGTGGTTGCCCAACAGGATTTCGTTRTCCTC, (SEQ ID NO:16)
GATCTTGAGGCTGGGAARCTGACATTCCTCAGT, (SEQ ID NO:17)
CACGTACTCGTAGGCCGAGTTSCCGGCGATGAA, (SEQ ID NO:18)
GCTGAGGTCAATCATGCGTTTGAAGAGGTAGTC, (SEQ ID NO:19)
YARGGCGATCATGCTGTCGACDGTRGAGATRCT, (SEQ ID NO:20)
CCTGAAGTCRGTRTTTTCCAGCGGGTCGATRTC, (SEQ ID NO:21)
CACATATTCATAGGCCGAGTTSCCGGCGATGAA, (SEQ ID NO:22)
CGCCACCGGCGAGATGCCGCATAGGCGACGGAG, (SEQ ID NO:23)
GCATGTCGTCCCTTCGACGTACACTTCCTGACG, (SEQ ID NO:24)
CGGGATGATGGTCAGCTCCTCGTAGCATTGGGC, (SEQ ID NO:25)
CTGCAGCCGCTTGTTCARCGAGCGGCCCTGATT, (SEQ ID NO:26)
ACGGTGGACCGCTATATGGTTGCACAGCAAGCC, (SEQ ID NO:27)
CGTCTGGATATTCACATCGGACTGGCTTGACGG, (SEQ ID NO:28)
GCGCGTTGTCAGGTCCAGCAGGTCCTGCTCCAC, (SEQ ID NO:29)
GAGGGCCGAAAGGACTCCAGCCAAGTGGGGGAT, (SEQ ID NO:30)
GTGGTAGGCCGATGAAGAAGAGAATAGGCTTTT, (SEQ ID NO:31)
CCTCAGCGCCTCCTCCGCCTCCTGGATGTAGCT, (SEQ ID NO:32)
TCGTTCCGGTATATCCGTAAACAGGTTGTACTC, (SEQ ID NO:33)
GGACCAGTAGGTAAAATCCGACAAGGAATATAT, (SEQ ID NO:34)
GCCCACCCGCTTGACGATAACCTCCGAGGTACG, (SEQ ID NO:35)
CTGGTGATACACATTTAGCTGCTGGATGGTGAT, (SEQ ID NO:36)
GCGACTGATGCCGTTCATGAGCGCCCGGCACAG, (SEQ ID NO:37)
GAAGATGTCCTCCACGTCCTCCCCGTACAGATG, (SEQ ID NO:38)
CTCCTCCCCGTCCAACGCCTTTTCCCCGAGCAC, and (SEQ ID NO:39)

GGGGGCGGCAAAGACCGACCCCACGAACATGCG. (SEQ ID NO:40)

2. A synthetic oligonucleotide useful as a capture probe in a sandwich hybridization assay for cytomegalovirus consisting of:
a first segment having a minimum length of about 25 nucoleotides and a maximum length of about 1000 nucleotides comprising a nucleotide sequence substantially complementary to a segment of cytomegalovirus nucleic acid; and
a second segment consisting of a nucleotide sequence which is substantially complementary to an oligonucleotide bound to a solid phase but not complementary to cytomegalovirus nucleic acid,
and optionally one or more non-complementary segments each consisting of a nucleotide sequence that is not complementary to cytomegalovirus nucleic acid;
wherein said nucleotide sequence substantially complementary to a segment of cytomegalovirus nucleic acid is selected from the group consisting of the sequences

| | |
|---|---|
| ACGCARYTCTTTCTGCGAGTAAAGTTCCAGTAC | (SEQ ID NO:41), |
| CATGATCTCYTCGAGRTCAAAAACGTTGCTGGA | (SEQ ID NO:42), |
| CTTTACCCGCTGCTTGTACGAGTTGAAYTCGCG | (SEO ID NO:43), |
| CGGYARCGGGTCGACTACCTTGTCCTCCACGTA | (SEQ ID NO:44), |
| GCTCATGAGGTCGTCCAGACCCTTGAGGTAGGG | (SEQ ID NO:45), |
| CTTTACCCGCTGCTTATACGAATTGAAYTCGCG | (SEO ID NO:46), |
| GCTGAGGGATGTGATGAGGTCGATGATCCTGTT | (SEQ ID NO:47), |
| GTTGAACACCGGGTTGTCCTCGAAAGCTTGAAT | (SEQ ID NO:48), |
| TTTGGTGTACATCTCGTTGCTTTCGTGGAGCTT | (SEQ ID NO:49) and |
| CGGACGTCGAATCTCCTCGAGAATATGCTTGAT | (SEQ ID NO:50). |

3. A set of synthetic oligonucleotides useful as amplifier probes in a sandwich hybridization assay for cytomegalovirus, comprising at least two different oligonucleotides, wherein each member of the set consists of
a first segment having a minimum length of about 25 nucleotides and a maximum length of about 1000 nucleotides comprising a nucleotide sequence substantially complementary to a segment of cytomegalovirus nucleic acid; and
a second segment consisting of a nucleotide sequence which is substantially complementary to an oligonucleotide multimer but not complementary to cytomegalovirus nucleic acid,
and optionally one or more non-complementary segments each consisting of a nucleotide sequence that is not complementary to cytomegalovirus nucleic acid;
wherein each said nucleotide sequence substantially complementary to a segment of cytomegalovirus nucleic acid is selected from the group consisting of the sequences

| | |
|---|---|
| CCGRTTGATGTARCYGCGCAACGTRTCRTAGGT | (SEQ ID NO:6), |
| CACACACCARGCYTCKGCGATYTGYGYYARCGC | (SEQ ID NO:7), |
| TTCCYTGAAGACCTCYAGGGWGCGCCGTTGATC | (SEQ ID NO:8), |
| YGAGAGAATRGCTGAYGGRTTGATCTTGCTRAG | (SEQ ID NO:9), |
| GAAACGCGCGGCAATCGGTTTGTTGTARATGGC | (SEQ ID NO:10), |
| CACGCAGCTGGCCARRCCCARRACATCACCCAT | (SEQ ID NO:11), |
| ACGCAGCACCTTRACGCTKGTTTGGTTRATRGT | (SEO ID NO:12), |
| GCAGCGTCCTGGCGAYTCYTTCACRTTCATATC | (SEQ ID NO:13), |
| GRCGAAATTAAAGATCACCACKGGTCGYGAGTA | (SEQ ID NO:14), |
| RCCCAGTTGACCGTACTGCACRTACGAGCTGTT | (SEQ ID NO:15), |
| GCGGTGGTTGCCCAACAGGATTTCGTTRTCCTC | (SEQ ID NO:16), |
| GATCTTGAGGCTGGGAARCTGACATTCCTCAGT | (SEQ ID NO:17), |

| | |
|---|---|
| CACGTACTCGTAGGCCGAGTTSCCGGCGATOAA | (SEQ ID NO:18) |
| GCTGAGGTCAATCATGCGTTTGAAGAGGTAGTC | (SEO ID NO:19), |
| YARGGCGATCATGCTGTCGACDGTRGAGATRCT | (SEQ ID NO:20), |
| CCTGAAGTCRGTRTTTTCCAGCGGGTCGATRTC | (SEQ ID NO:21), |
| CACATATTCATAGGCCGAGTTSCCGGCGATGAA | (SEQ ID NO:22), |
| CGCCACCGGCGAGATGCCGCATAGGCGACGGAG | (SEQ ID NO:23), |
| GCATGTCGTCCCTTCGACGTACACTTCCTGACG | (SEQ ID NO:24), |
| CGGGATGATGGTCAGCTCCTCGTAGCATTGGGC | (SEQ ID NO:25), |
| CTGCAGCCGCTTGTTCARCGAGCGGCCCTGATT | (SEQ ID NO:26), |
| ACGGTGGACCGCTATATGGTTGCACAGCAAGCC | (SEQ ID NO:27), |
| CGTCTGGATATTCACATCGGACTGGCTTGACGG | (SEQ ID NO:28), |
| GCGCGTTGTCAGGTCCAGCAGGTCCTGCTCCAC | (SEQ ID NO:29), |
| GAGGGCCGAAAGGACTCCAGCCAAGTGGGGGAT | (SEQ ID NO:30), |
| GTCCTAGGCCGATCAAGAAGAGAATAGGCTTTT | (SEQ ID NO:31), |
| CCTCAGCGCCTCCTCCGCCTCCTGGATGTAGCT | (SEQ ID NO:32), |
| TCGTTCCGGTATATCCGTAAACAGGTTGTACTC | (SEQ ID NO:33), |
| GGACCAGTAGGTAAAATCCGACAAGGAATATAT | (SEQ ID NO:34), |
| GCCCACCCGCTTGACGATAACCTCCGAGGTACG | (SEQ ID NO:35), |
| CTGGTGATACACATTTAGCTGCTGGATGGTGAT | (SEQ ID NO:36), |
| GCGACTGATGCCGTTCATGAGCGCCCGCCACAG | (SEQ ID NO:37), |
| GAAGATGTCCTCCACGTCCTCCCCGTACAGATG | (SEQ ID NO:38), |
| CTCCTCCCCGTCCAACGCCTTTTCCCCGAGCAC | (SEQ ID NO:39) and |
| GGGGGCGGCAAAGACCGACCCCACGAACATGCG | (SEQ ID NO:40). |

4. The set of synthetic oligonucleotides of claim 3, wherein each said second segment comprises

AGGCATAGGACCCGTGTCTT (SEQ ID NO: 51).

5. A set of synthetic oligonucleotides useful as capture probes in a sandwich hybridization assay for cytomegalovirus, comprising at least two different oligonucleotides, wherein each member of the set consists of
   a first segment having a minimum length of about 25 nucleotides and a maximum length of about 1000 nucleotides comprising a nucleotide sequence substantially complementary to a segment of cytomegalovirus nucleic acid; and
   a second segment consisting of a nucleotide sequence which is substantially complementary to an oligonucleotide bound to a solid phase but not complementary to cytomegalovirus nucleic acid,
   and optionally one or more non-complementary segments each consisting of a nucleotide sequence that not complementary to cytomegalovirus nucleic acid;
   wherein each said nucleotide sequence substantially complementary to a segment of cytomegalovirus nucleic acid is selected from the group consisting sequences

| | |
|---|---|
| ACGCARYTCTTTCTGCGAGTAAAGTTCCAGTAC | (SEQ ID NO:41), |
| CATGATCTCYTCGAGRTCAAAAACGTTGCTGGA | (SEQ ID NO:42), |
| CTTTACCCGCTGCTTGTACGAGTTGAAYTCGCG | (SEQ ID NO:43), |
| CGGYARCGGGTCGACTACCTTGTCCTCCACGTA | (SEQ ID NO:44), |
| GCTCATGAGGTCGTCCAGACCCTTGAGGTAGGG | (SEQ ID NO:45), |
| CTTTACCCGCTGCTTATACGAATTGAAYTCGCG | (SEQ ID NO:46), |
| GCTGAGGGATGTGATGAGGTCGATGATCCTGTT | (SEQ ID NO:47), |
| GTTGAACACCGGGTTGTCCTCGAAAGCTTCAAT | (SEQ ID NO:48), |
| TTTGGTGTACATCTCGTTGCTTTCGTGGAGCTT | (SEQ ID NO:49) and |
| CGGACGTCGAATCTCCTCGAGAATATGCTTGAT | (SEQ ID NO:50). |

6. The set of synthetic oligonucleotides of claim 5, wherein each said second segment comprises

CTTCTTTGGAGAAAGTGGTG (SEQ ID NO: 53).

7. A solution sandwich hybridization assay for detecting the presence of cytomegalovirus in a sample, comprising (a) contacting the sample under hybridizing conditions with (i) amplifier probes comprising the set of synthetic oligonucleotides of claim 5 and (ii) a set of capture probe oligonucleotides wherein there is a molar excess of amplifier probes and of capture probes over analyte nucleic acid in the sample;

(b) contacting the product of step (a) under hybridizing conditions with said oligonucleotide bound to the solid phase;

(c) thereafter separating materials not bound to the solid phase;

(d) contacting the bound product of step (c) under hybridization conditions with a nucleic acid multimar, said multimar comprising at least one oligonucleotide segment that is substantially complementary to the second segment of the amplifier probe polynucleotide and a multiplicity of second oligonucleotide segments that are substantially complementary to a labeled oligonucleotide;

(e) removing unbound multimer;

(f) contacting under hybridizing conditions the solid phase complex product of step (e) with the labeled oligonucleotide;

(g) removing unbound labeled oligonucleotide; and (h) detecting the presence of label in the solid phase complex product of step (g) and, thereby, detecting the presence of virus in the sample;

wherein said set of capture probe oligonucleotides comprises at least two different oligonucleotides, wherein each member of the set consists of
   a first segment having a minimum length of about 25 nucleotides and a maximum length of about 1000 nucleotides comprising a nucleotide sequence substantially complementary to a segment of cytomegalovirus nucleic acid; and a second segment consisting of a nucleotide sequence which is substantially complementary to an oligonucleotide bound to a solid phase but not complementary to cytomegalovirus nucleic acid, and optionally one or more non-complimentary segments each consisting of a nucleotide sequence that is not complementary to cytomegalovirus nucleic acid;

wherein each said nucleotide sequence substantially complementary to a segment of cytomegalovirus nucleic acid is selected from the group consisting of the sequences

| | |
|---|---|
| ACGCARYTCTTTCTGCGAGTAAAGTTCCAGTAC | (SEG ID NO:41), |
| CATGATCTCYTCGAGRTCAAAAACGTTGCTGGA | (SEQ ID NO:42), |
| CTTTACCCGCTGCTTGTACGAGTTGAAYTCGCG | (SEQ ID NO:43), |
| CGGYARCGGGTCGACTACCTTGTCCTCCACGTA | (SEQ ID NO:44), |
| GCTCATGAGGTCGTCCAGACCCTTGAGGTAGGG | (SEQ ID NO:45), |
| CTTTACCCGCTGCTTATACGAATTGAAYTCGCG | (SEQ ID NO:46), |
| GCTGAGGGATGTGATGAGGTCGATGATCCTGTT | (SEQ ID NO:47), |
| GTTGAACACCGGGTTGTCCTCGAAAGCTTGAAT | (SEQ ID NO:48), |
| TTTGGTGTACATCTCGTTGCTTTCGTGGAGCTT | (SEG ID NO:49) and |
| CGGACGTCGAATCTCCTCGAGAATATGCTTGAT | (SEQ ID NO:50). |

8. A kit for the detection of cytomegalovirus in a sample comprising in combination
   (i) a set of amplifier probe oligonucleotides comprising the set of synthetic oligonucleotides of claim 5;
   (ii) a set of capture probe oligonucleotides;
   (iii) a nucleic acid multimar, said multimer comprising at least one oligonucleotide segment that is substantially complementary to the second segment of the amplifier probe polynucleotide and a multiplicity of second oligonucleotide segments that are substantially complementary to a labeled oligonucleotide; and
   (iv) a labeled oligonucleotide; wherein said set of capture probe oligonucleotides comprises at least two different oligonucleotides, wherein each member of the set consists of
   a first segment having a minimum length of about 25 nucleotides and a maximum length of about 1000 nucleotides comprising a nucleotide sequence substantially complementary to a segment of cytomegalovirus nucleic acid; and
   a second segment consisting of a nucleotide sequence which is substantially complementary to an oligonucleotide bound to a solid phase but not complementary to cytomegalovirus nucleic acid, and optionally one or more non-complementary segments each consisting of a nucleotide sequence that is not complementary to cytomegalovirus nucleic acid;

wherein each said nucleotide sequence substantially complementary to a segment of cytomegalovirus nucleic acid is selected from the group consisting of the sequences

| | |
|---|---|
| ACGCARYTCTTTCTGCGAGTAAAGTTCCAGTAC | (SEQ ID NO:41), |
| CATGATCTCYTCGAGRTCAAAAACOTTGCTGGA | (SEQ ID NO:42), |
| CTTTACCCGCTCCTTGTACGAGTTGAAYTCGCG | (SEQ ID NO:43), |
| CGGYARCGGGTCGACTACCTTGTCCTCCACGTA | (SEQ ID NO:44), |
| GCTCATGACGTCGTCCAGACCCTTGAGGTAGGG | (SEQ ID NO:45), |
| CTTTACCCGCTGCTTATACGAATTGAAYTCGCG | (SEQ ID NO:46), |
| GCTGAGGGATGTGATCAGGTCGATGATCCTGTT | (SEQ ID NO:47), |
| GTTGAACACCGGGTTOTCCTCGAAARCTTGAAT | (SEQ ID NO:48), |
| TTTGGTGTACATCTCGTTGCTTTCGTGRAGCTT | (SEQ ID NO:49) and |
| CGGACGTCGAATCTCCTCGAGAATATGCTTGAT | (SEQ ID NO:50). |

9. The kit of claim 8, said kit further comprising instructions for the use thereof.

* * * * *